United States Patent [19]

Cook et al.

[11] 4,265,122
[45] May 5, 1981

[54] NONDESTRUCTIVE TESTING APPARATUS AND METHOD UTILIZING TIME-DOMAIN RAMP SIGNALS

[75] Inventors: Billy D. Cook; Eduardo Cavanagh, both of Houston, Tex.

[73] Assignee: University of Houston, Houston, Tex.

[21] Appl. No.: 32,176

[22] Filed: Apr. 23, 1979

[51] Int. Cl.³ .................... G01N 29/04; G02B 5/14
[52] U.S. Cl. .................................. 73/627; 73/644; 73/655; 350/96.13
[58] Field of Search ............. 73/624, 627, 632, 655, 73/644; 350/96.13, 96.24, 96.29, 358

[56] References Cited

U.S. PATENT DOCUMENTS

| | | | |
|---|---|---|---|
| 3,297,875 | 1/1967 | Garwin et al. | 350/96.29 |
| 3,771,856 | 11/1973 | Eschler | 350/358 |
| 3,856,378 | 12/1974 | Brandt et al. | 350/96.3 |
| 3,903,496 | 9/1975 | Stimler | 350/96.24 |
| 3,903,497 | 9/1975 | Stimler et al. | 350/96.24 |
| 3,916,182 | 10/1975 | Dabby et al. | 350/96.13 |
| 3,931,595 | 1/1976 | Isaacs et al. | 350/96.13 |
| 4,019,373 | 4/1977 | Freeman et al. | 73/644 |
| 4,068,191 | 1/1978 | Zemon et al. | 350/96.13 |
| 4,070,091 | 1/1978 | Taylor et al. | 350/96.29 |
| 4,162,397 | 7/1979 | Bucaro et al. | 73/655 |

OTHER PUBLICATIONS

M. B. Moffett et al.; "Model for Parametric Acoustic Sources," *J. Acoust. Soc. Am.*, vol. 61, No. 2, pp. 325-337, Feb. 1977.
J. H. Cole et al.; "Fiber-Optic Detection of Sound," *J. Acoust. Soc. Am.*, vol. 62, No. 5, pp. 1136-1138, Nov. 1977
J. A. Bucaro et al.; "Fiber-Optic Hydrophone," *J. Acoust. Soc. Am.*, vol. 62, No. 5, pp. 1302-1304, Nov. 1977.
J. H. Hunter et al.; "Acoustic Backscattering From Thin Air-Filled Spherical Shells in Water," *J. Acoust. Soc. Am.*, vol. 62, No. 5, pp. 1139-1143, Nov. 1977.
J. D. Young, "Radar Imaging From Ramp Response Signatures," IEEE Transactions on Attenas and Propogation, vol. AP-24, pp. 276-282, 1977.
R. D. Strattan, "Target Identification From Radar Signatures," IEEE International Conference on Acoustics, Speech, and Signal Processing, pp. 223-227, Apr. 1978.

*Primary Examiner*—Stephen A. Kreitman
*Attorney, Agent, or Firm*—Arnold, White & Durkee

[57] ABSTRACT

Disclosed is an apparatus and method for nondestructive testing of structures where the apparatus includes a transducer for generating an ultrasonic acoustic signal, a nonlinear medium for parametrically generating a special, ramp, waveform, and an acousto-optic broadband receiver for detecting a reflected signal from the test structure. A homodyne interferometer is provided to measure the change of refractive index of the acousto-optic receiver, and generates an electrical signal representative of the reflected acoustic signal. Signature analysis techniques are utilized to evaluate the reflected waveform to determine the characteristics of the structural defects.

21 Claims, 6 Drawing Figures

RAMP SIGNAL

BROADBAND RESPONSE SIGNAL

NONDESTRUCTIVE TESTING APPARATUS AND METHOD UTILIZING TIME-DOMAIN RAMP SIGNALS

BACKGROUND OF THE INVENTION

This invention relates to a nondestructive testing apparatus and method, and more specifically to an apparatus and method utilizing parametric generation, acousto-optic reception and signature analysis for analyzing flaws in structures.

It is a continuing effort to produce and design products that are materially sound with a high degree of quality and reliability. With the advent of manufacturing plants and structures designed for operations that involve dangerous or expensive processes the engineering approach of overdesign to include large safety factors became unacceptable and the need arose for a more direct approach for nondestructive evaluation of materials.

Methods of nondestructive evaluation (NDE) include magnetic induction, flux leakage, eddy current, liquid penetrant X-ray radiography and ultrasonic testing. Since the present invention lies in the field of ultrasonic testing of structures, only that field will be addressed.

Forms of nondestructive testing using ultrasonic signals include pulse echo methods and pitch and catch methods. In the pulse echo methods of nondestructive testing, a single transducer, conventionally a piezoelectric crystal material, is utilized to transmit and receive an ultrasonic signals. Piezoelectric crystals are utilized and operated at or near their resonance frequency to enhance their radiation efficiencies and receiving sensitivities. However, most attempts to achieve a uniform output, both in amplitude and phase, over a wide range of frequencies is usually done by damping the resonance of the crystals. This damping results in lower efficiencies in generation and lower sensitivities in reception. Optimally, methods enabling the evaluation and analysis of a large band of frequencies, 0.1 to 10 MHz for example, are desired since the greater number of frequencies available, the more that may be interpreted from the reflected signals.

The pitch and catch methods of ultrasonic testing are fundamentally using the same principals as the pulse echo methods except two transducers are provided; one for transmitting the ultrasonic signal and one for receiving the signal after it has been applied to a test structure. The major disadvantages found in standard ultrasonic devices is in the constraints of the transducers which are not capable of generating and detecting boardband ultrasonic pulses.

It is generally a difficult manufacturing task to make a broadband receiver capable of handling 1 to 10 MHz, the device would be extremely small since the size must be smaller than one wavelength.

The present invention overcomes this disadvantage through the use of a transducer utilizing parametric generation and broadband reception with a method of analysis analogous to novel radar signature analysis.

Studies in experimental scattering in radar indicate that particular waveshapes, such as ramp functions for example, for radiating and interrogating the signal, produce back scattered waveshapes which may be interpreted by a technician to analyze the overall shape of the object detected. In radar scattering studies the information that may be derived from ramp pulse radiating signals includes object cross sectional area, total object volume, and object length along the line of sight. In a nondestructive testing environment the object to be detected in the test structure is the flaw or hole in the test structure analogous to a missle in the atmosphere, for example. Experimental verification of these radar scattering theories are found in a paper entitled "Radar Imaging From Ramp Response Signatures" by Johnathan D. Young, IEEE Transactions on Antennas and Propagation, Vol. AP-24, page 276–282, 1977. The critical obstacle in this method of target identification is in the generation of a proper waveform to interrogate the object to be detected. Since a ramp waveform is desirable, Young in his experimental studies artificially generated a ramp pulse utilizing ten distinct frequency signals.

Analysis of the back scattered signal from the detected object yields information about the detected object beyond mere location. The information interpreted from the waveform height is proportional to the cross sectional area versus the distance along the line of sight of the object. Further, the integral of the waveform is found to be proportional to the total object volume. Also, the object length along the line of sight may be interpreted from the zero crossings of the waveform.

Conventional piezoelectric and other crystal transducers are not capable of generating an ultrasonic signal pulse that is broadband in a useful frequency range. Low frequency envelope functions are known to be generated in a nonlinear absorbtion medium. These absorbtive and nonlinear effects on an ultrasonic signal, produce an effect known as parametric generation or self-demodulation which allows production of a signal at useful frequencies much lower than the frequency of the electrical signal applied to the medium. Typically, an intense ultrasonic frequency signal consisting of an ultrasonic with a defined modulation is generated by a piezoelectric crystal to propagate through an absorbing nonlinear medium. The nonlinear medium will absorb the ultrasonic frequency carrier and the nonlinear interaction will generate a signal of lower frequencies whose shape can be controlled by changing the original modulation function.

The main objective in any nondestructive testing apparatus and method is to provide as much information about the test structure as possible. The test structure may take the form of an oil well casing, a nuclear power reactor, jet and space aircraft, and even the human body. Conventional ultrasonic nondestructive evaluation techniques and apparatus provide information relating only to the location of the defect or flaw. Conventional transducers have an inherent limitation of being narrowband thus reducing the number of frequencies that may be evaluated. Further, useful low frequency signals normally have a spatial spread that is unacceptable to detect flaws that are adjacent to one another. This spatial spread reduces the overall sensitivity of the device and reliability of the test results.

SUMMARY OF THE INVENTION

A nondestructive testing apparatus and method utilizing ramp signals is provided by the present invention for detecting flaws and other defects in test structures and further characterizing those flaws and defects by waveform signature analysis. To facilitate interrogation of the test structure, a transducer is provided incorporating self-demodulation techniques and broadband reception. Generation of the devised waveform is to be produced by self-demodulation of an intense, ultrasonic signal propagating through a region of nonlinear absorbing material. The resulting waveshape is controlled by the modulation of the electrical carrier signal driving the transducer producing the ultrasonic acoustic waves. Thus, a nondestructive testing device capable of wide bandwidth at desired frequencies with a smaller beam spread than a conventional device is provided.

The nondestructive testing apparatus includes a pulse generator for generating an ultrasonic signal, for example. The apparatus further includes an acoustic parametric transducer having a support-housing, and a conventional transducer, such as a piezoelectric crystal, electrically connected to the pulse generator for generating an acoustic signal having an ultrasonic frequency carrier with a defined modulation. A nonlinear absorbing medium is also provided adjacent to the conventional transducer for parametrically generating a low frequency envelope or ramp waveform to be transmitted to a nearby test structure.

In order to effectively analyze the frequencies of the backscattered ramp waveform, a broadband nonresonant receiver is utilized and disposed within the support-housing of the conventional transducer and nonlinear medium.

The broadband nonresonant receiver may be an acousto-optic broadband receiver whereby the induced change in refraction of index of an optical fiber at the periphery of the support, adjacent to a test structure is sensed and compared in a homodyne or heterodyne detection device. The electrical signal generated by a photodetector is demodulated and displayed on a cathode ray oscilloscope; the signal is representative of the backscattered acoustic signal. In the heterodyne device an optical frequency shifter generates a carrier resulting in a frequency modulated signal at the photodetector. An alternative embodiment of the nonresonant broadband receiver may be a polyvinylfluoride acoustically sensitive strip, electrically connected to a proper display mechanism.

The acoustic parametric transducer provided in the nondestructive testing apparatus may further be totally encapsulated having the pulse generator and homodyne detection device external to the housing and attached to the conventional transducer and optical-fiber coil by electrical and optical leads respectively.

BRIEF DESCRIPTION OF THE DRAWINGS

The features and advantages of the instant invention will become more apparent upon reading the following detailed description in reference to the drawings in which.

DETAILED DESCRIPTION OF THE DRAWINGS

In its basic configuration, one form of the acoustic-parametric transducer provided in the instant invention utilizes a conventional transducer for producing an ultrasonic acoustic signal, and a nonlinear absorbing medium for self-demodulation or parametric generation of a special waveform to be transmitted to a testing structure for flaw detection. The reflected signal is sensed by a nonresonant receiver having wide bandwidth reception. This transducer configuration enables nondestructive testing of structures by radar signature analysis for evaluating location, volume, cross section and length of the defect.

Figure 1:
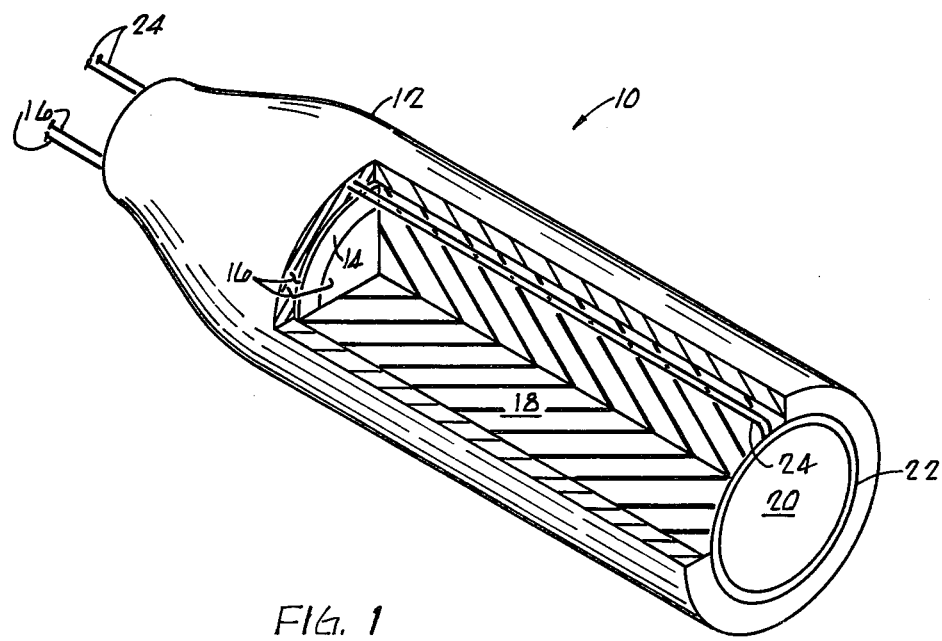
FIG. 1 is a diagrammatic view showing the basic configuration of one form of the acoustic-parametric transducer in accordance with the instant invention.

Referring now to the figures and more particularly to FIG. 1, an encapsulated transducer 10 is illustrated. The transducer 10 includes a support member 12 that may be an enclosed housing.

Included in the support member 12 is a conventional piezoelectric transducer 14. The piezoelectric transducer 14 may comprise a piezoelectric crystal such as Lithium Niobate, for example. The piezoelectric transducer 14 is electrically connected by electrical leads 16 to a high frequency pulse generator (not shown). A further characteristic of the piezoelectric transducer 14 is that it has a high natural resonance frequency, on the order of 25 MHz. A specific electrical signal is delivered through the leads 16 to the piezoelectric transducer 14 with a modulated high frequency carrier signal.

A nonlinear absorbing media 18 is provided adjacent to the piezoelectric crystal transducer 14 in the housing 12. The nonlinear absorbing media 18 is disposed in the housing between the piezoelectric transducer 14 and a radiating surface 20 of the housing 12. The nonlinear absorbing media 18 has the properties of being absorptive to the high frequencies and "nonlinear" in responding to the acoustic waves delivered by the conventional piezoelectric crystal transducer 14. Although all known materials exhibit some degree of nonlinearity, silicone rubber is one example of a nonlinear medium used for producing lower frequency signals. The length of the material may be chosen to achieve the proper proportion of absorption and nonlinear effect, although this length is not a critical factor in the overall effectiveness of the transducer performance.

Figure 2:
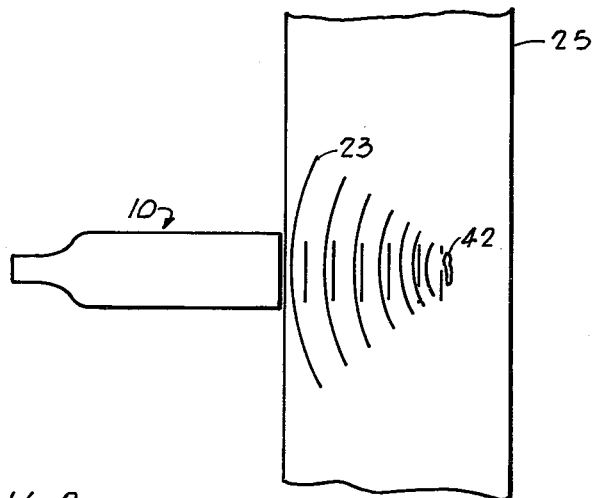
FIG. 2 is a schematic view of the acoustic-parametric transducer and test structure, in accordance with the instant invention.

The transducer 10 also includes a nonresonant broadband receiver, a specific embodiment is shown in FIG. 1 as an acousto-optic receiver. The acousto-optic receiver includes a fiber-optic detecting coil 22 located at the periphery of the housing 12 adjacent to the transducer radiating surface 20. The fiber-optic detecting coil 22 is located to intercept the acoustic signal 23 reflected from the test structure 25, as better illustrated in FIG. 2. The fiber-optic detecting coil is also connected to a homodyne detection device, illustrated in FIG. 3 and described hereinbelow, by fiber-optic leads 24.

The incoming acoustic signal 23 changes the index of refraction of the fiber coil 22. This change is sensed by the optical arrangement illustrated in FIG. 3. Fiber optics used in this manner have been demonstrated to have broadband characteristics. Further, their sensitivities have been theoretically calculated and experimentally verified to be equal or greater than piezoelectric receivers. One such demonstration of these principles may be found in an article entitled "Fiber-Optic Detection of Sound" by Cole, Johnson and Bhuta, J. Acoust, Soc. Am. Vol. 62, No. 5, November 1977. Most sensitivity occurs when the optical fiber is designed to be a "single-mode" fiber and this is one example of the type of optical fiber that may be used in the broadband receiver of one form of the instant invention.

Figure 3:
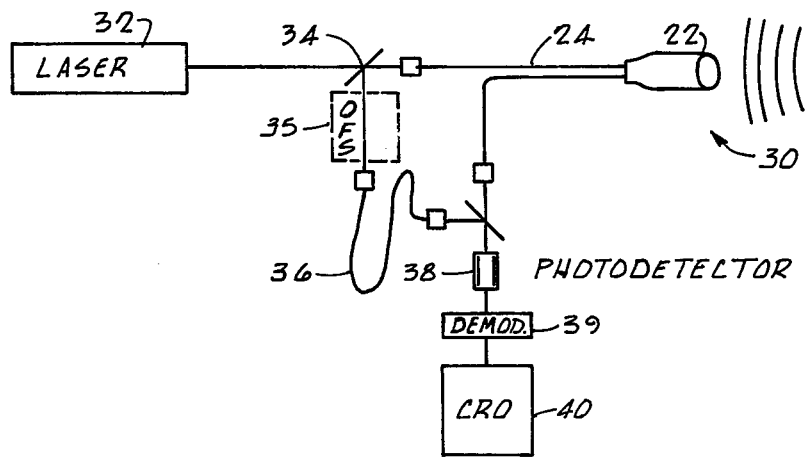
FIG. 3 is a diagrammatic view of a homodyne/heterodyne detection scheme for detecting ultrasound produced changes of refractive index, in accordance with the instant invention.

FIG. 3 illustrates a homodyne/heterodyne detection device 30 utilized in conjunction with the fiber optic coil 22 shown in FIG. 1 to effect a broadband nonresonant receiver. The homodyne/heterodyne detection device 30 includes a coherent light source 32, that may be a laser or light emitting diode for example. Part of the collimated light beam is deflected by a mirror-like surface 34 into a reference optical fiber 36 while the remainder is delivered to the fiber-optic coil 22 via the coil leads 24. For the detection device 30 to be a heterodyne system, an optical frequency shifter (OFS) 35 (shown as an optional feature by the dotted lines) must be utilized to obtain a frequency modulated carrier signal. The detection device 30 defaults to a homodyne system without the OFS 35, producing an amplitude modulated signal. The optical frequency shifter (OFS) 35, is inserted in either the optical path between the mirror-like surface 34 and either optical fiber 24 or 36. The optical outputs of both the fiber lead 24 and the reference fiber 36 are delivered to a photodetector 38. The optical frequency shifter 35 provides a carrier signal resulting in a frequency modulated signal at the photodetector. The electrical signal delivered by the photodetector is a representation of the reflected acoustic signal from the test structure 25. This electrical signal is demodulated by a demodulator 39 in both the homodyne and heterodyne detection devices for reducing nonlinearities and frequency demodulation, respectively. This signal is displayed on a cathode ray oscilloscope 40 for purposes of radar signature analysis for characterizing any flaws within the test structure.

Figure 4A:
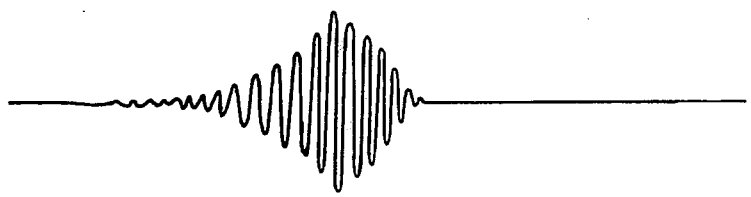
FIG. 4A is a graphical representation of a broadband signal delivered to the nonlinear medium of the acoustic-parametric transducer, in accordance with the instant invention.
Figure 4B:
FIG. 4B is a graphical representation of a ramp signal parametrically generated in the acoustic parametric transducer, in accordance with the instant invention.
Figure 4C:
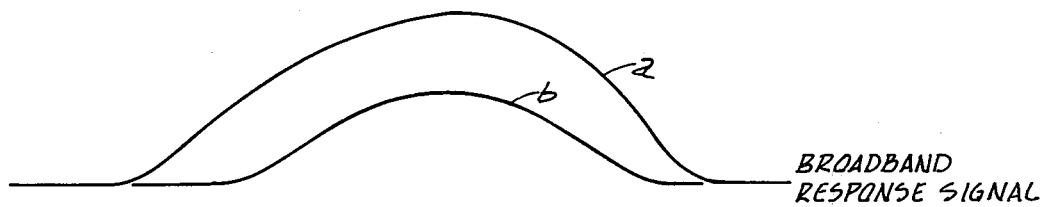
FIG. 4C is a graphical representation of two broadband response signals received from a test structure, in accordance with the instant invention.

Operationally, an electrical pulse is delivered to the piezoelectric transducer 14 which then delivers to the nonlinear absorbing medium 18 an acoustic signal having a high frequency carrier. A waveform of the ultrasonic acoustic pulse is shown in FIG. 4A. This intense ultrasonic signal consisting of a high frequency carrier with a defined modulation propagates through the nonlinear medium 18 to parametrically generate a special waveform having a waveshape useful in radar signature analysis. At the exit plane of the transducer 10, the high frequency carrier wave will be absorbed; however, the nonlinear processes of the medium 18 will have generated a signal of lower frequencies whose shape is controlled by changing the original modulation function. This low frequency waveform as illustrated in FIG. 4B is a ramp function. The ramp signal is then delivered to a test structure 25 where it will be reflected by any defects in that structure, such as the defect 42 shown in FIG. 2. The fiber optic detecting coil 22 will receive the reflected acoustic signal, and through the homodyne/heterodyne detection device generate a representative ultrasonic signal from the changes in the refraction of index of the fiber-optic coil 22. An example of the reflected acoustic waveform is illustrated in the graph of FIG. 4C. The "A" curve in FIG. 4C represents a defect having a larger volume and greater length and cross section than the defect demonstrated by curve "B". These characteristics of the defect are approximated from the waveform, area, zero-crossing and height, respectively.

The combination of parametric generation and fiber-optic detection has several distinct advantages over conventional transducers used for pulse echo and pitch and catch methods of nondestructive testing. The transducer 10 of the instant invention, for example, has a frequency response that is not controlled by the resonance of the piezoelectric crystal as in a conventional piezoelectric transducer used as a receiver. Further, the electrical driving signal is completely decoupled from the reception circuit; consequently the electrical overload of the receiving circuit is eliminated. Also, the spatial spread of the radiating beam from a parametric transducer is narrower and not as frequency sensitive as in a conventional transducer. Most importantly, pulse shapes such as the "ramp" can be generated and refined by an external modulating control circuit.

This ability to generate desired pulse shapes as the ramp function enables analysis of elastic wave scattering in a test structure analogous to radar scattering and signature analysis. Evaluating the reflected waveform as displayed in the cathode ray oscilloscope 40 of the homodyne/heterodyne detection device 30 shown in FIG. 3 can yield the following information about a void or defect in the test structure: (a) cross sectional area versus distance along the line of sight; (b) total object volume; and (c) object length along the line of sight.

The information of the target geometry is directly visable in the waveform of the returning reflected signal. The amplitude of the waveform versus time is approximately proportional to the "target profile function". This profile function is defined as the time-domain waveform equal to the target cross sectional area along the line of sight with adjusted time scale related to velocity of sound. With the broadband transducer scheme capable of generating and receiving undistorted ultrasonic waveforms, this time profile function is directly viewable on an oscilloscope screen. It has also been established experimentally that the volume of the defect is proportional to the integral of the waveform. Further, the length of the defect has been found to approximate the zero crossing of the waveform. As a result a trained nondestructive examining technician is capable of instantaneous decision on the size, orientation and approximate volume of the flaw. A major advantage in this method of analysis of the characteristics of a structural flaw is that it is performed in real time.

While the present invention has been described and illustrated with respect to a specific embodiment; it will be understood to those skilled in the art that many modifications and changes may be made without departing from the spirit and scope of the invention for example, the ramp pulse radiating signal may be generated by combining electrical signals of varying frequencies or pulsing a piezoelectric transducer with different shaped signals as defined in the appended claims.

What is claimed is:
1. A nondestructive testing apparatus comprising:
    a high frequency electrical pulse generator;
    a first transducer for producing and detecting broadband pulses of ultrasonic energy including:
        a support, a second transducer located on said support, electrically connected to said generator, for generating an acoustic signal with a modulated ultrasonic carrier signal, a nonlinear absorbing material disposed within said support and located adjacent to said first transducer for absorbing said carrier signal and parametrically generating a low frequency signal envelope having a waveform dependent upon said modulation, said low frequency signal envelope applied to a test structure for evaluation of defects, a nonresonant broadband receiver disposed on said support for receiving a reflected signal response from said structure; and a display for viewing and evaluating said reflected response.

2. A nondestructive testing apparatus as set forth in claim 1 wherein said second transducer comprises a piezoelectric crystal for generating an acoustic signal.

3. A nondestructive testing apparatus as set forth in claim 1 wherein said nonlinear absorbing material comprises silicone rubber.

4. A nondestructive testing apparatus as set forth in claim 1 wherein said nonresonant broadband receiver comprises an acousto-optic receiver.

5. A nondestructive testing apparatus as set forth in claim 4 wherein said acousto-optic receiver includes a fiber-optic coil located at the periphery of said support and, a homodyne detection device connected to said coil by optical leads.

6. A nondestructive testing apparatus as set forth in claim 5 wherein said homodyne detection device detects changes of the refractive index of said fiber-optic coil produced by said reflected signal, and includes; a coherent light source for suitably introducing a light beam into the optical fiber leads, a reference optical fiber, receiving reflected light from said coherent light source, a photodetector for sensing the optical outputs of both the fiber-optic coil and the reference fiber, and a demodulator electrically connected to said photodetector for reducing nonlinearities in said optical outputs, said demodulator delivering an electrical signal representative of said reflected signal.

7. A nondestructive testing apparatus as set forth in claim 1 wherein said nonresonant broadband receiver comprises a strip of polyvinylfluoride, acoustically sensitive and electrically connected to said display.

8. A nondestructive testing apparatus as set forth in claim 4 wherein said acoustic-optic receiver includes a heterodyne detection device having an optical frequency shifter for frequency modulating said reflected signal response.

9. A method of nondestructive testing comprising the steps of:

electrically generating an intense acoustic signal with a modulated ultrasonic carrier signal;

parametrically generating a low frequency signal envelope by passing said ultrasonic acoustic signal through a nonlinear absorbing medium, said low frequency signal envelope having a waveform dependent upon said modulation;

applying said low frequency signal to a test structure for the purpose of evaluating flaws therein;

detecting a reflected signal backscattered from said test structure; and evaluating the waveform of said reflected signal for the location, cross-sectional area, volume, and length of any flaws within the test structure using signature analysis.

10. A method of nondestructive testing as set forth in claim 9 wherein the step of electrically generating an acoustic signal includes generating a carrier frequency in the range of 20 to 50 MHz.

11. A method of nondestructive testing as set forth in claim 9 wherein the step of parametrically generating a low frequency signal envelope includes absorbing said carrier frequency signal to obtain a low frequency signal envelope in the range of 1 to 10 MHz.

12. A method of nondestructive testing as set forth in claim 9 wherein the step of evaluating said reflected signal includes measuring the height of said waveform, whereby said height is proportional to the cross-sectional area of said flaw.

13. A method of nondestructive testing as set forth in claim 9 wherein the step of evaluating said reflected signal includes calculating the integral of said waveform, whereby said integral is proportional to the volume of said flaw.

14. A method of nondestructive testing as set forth in claim 9 wherein the step of evaluating said reflected signal includes determining the zero crossings of said waveform, whereby the distance between said zero crossings is substantially equal to the length of said flaws.

15. A nondestructive testing apparatus comprising:
a high frequency electrical pulse generator;
means for producing and detecting broadband pulses of ultrasonic energy including:
a support,
a transducer located on said support, electrically connected to said generator, for generating an acoustic signal with a modulated ultrasonic carrier signal,
a nonlinear absorbing material disposed within said support and located adjacent to said first transducer for absorbing said carrier signal and parametrically generating a low frequency signal envelope having a waveform dependent upon said modulation, said low frequency signal envelope applied to a test structure for evaluation of defects,
a nonresonant broadband receiver disposed on said support for receiving a reflected signal response from said structure; and,
a means for evaluating said reflected response.

16. A nondestructive testing apparatus comprising:
a high frequency electrical pulse generator;
means for producing and detecting broadband pulses of ultrasonic energy including:
a support,
a transducer located on said support, electrically connected to said generator, for generating an acoustic signal with a modulated ultrasonic carrier signal,
means for generating a time-domain acoustic ramp signal in response to said modulated acoustic signal disposed within said support and located adjacent to said transducer, said ramp signal applied to a test structure for evaluation of defects,
a nonresonant broadband receiver disposed on said support for receiving a deflected signal response from said structure; and,
means for evaluating said reflected response.

17. A nondestructive testing apparatus comprising:

an electrical pulse generator; means for producing and detecting broadband pulses of ultrasonic energy including:

a support, means for generating a time-domain acoustic ramp signal, electrically connected to said generator, and disposed within said support, said ramp signal dependent upon the shape of said pulse from said pulse generator, and said ramp signal applied to a test structure for evaluation of defects, a nonresonant broadband receiver disposed on said support for receiving a reflected signal response from said structure; and, means for evaluating said reflected response.

18. In a nondestructive testing apparatus for ultrasonically testing structures for defects using a pulse generator and a means for evaluating reflected signals, including, a means for producing and detecting broadband pulses of ultrasonic energy comprising:

a support, means for generating a time-domain acoustic ramp signal in response to electrical pulses from said generator, disposed within said support, said ramp signal dependent upon the shape of said electrical pulse and applied to said test structure for evaluation of said defects; and, a nonresonant broadband receiver disposed on said support for receiving a reflected signal response from said structure.

19. A method of nondestructive testing comprising the steps of:

electrically generating an acoustic signal with a modulated ultrasonic carrier signal;

parametrically generating an acoustic ramp signal by passing said ultrasonic acoustic signal through a nonlinear absorbing medium, said ramp signal having a waveform dependent upon said modulation;

applying said low frequency signal to a test structure for purposes of evaluating flaws therein;

detecting a reflected signal back-scattered from said test structure; and evaluating said waveform of said reflected signal for the location, cross-sectional area, volume, and length of any flaws within the test structure using signature analysis.

20. A method of nondestructive testing comprising the steps of:

generating an electrical pulse having a predefined shape;

generating a time-domain acoustic ramp signal in response to said electrical pulse;

applying said ramp signal to a test structure for the purpose of evaluating flaws therein;

detecting a reflected signal back-scattered from said test structure; and, evaluating said waveform of said reflected signal for the location, cross-sectional area, volume and length of any flaws within the test structure using signature analysis.

21. A method of nondestructive testing comprising the steps of: electrically generating an acoustic signal with a modulated ultrasonic carrier signal;

parametrically generating a low frequency signal envelope by passing said ultrasonic acoustic signal through a non-linear absorbing medium, said low frequency signal envelope having a waveform dependent upon said modulation;

applying said low frequency signal to a test structure for the purpose of evaluating flaws therein;

detecting a reflecting signal back-scattered from said test structure wherein said step of detecting said reflected signal includes measuring the change in the refractive index of an optical fiber resulting from the presence of said reflected signal; and, evaluating the waveform of said reflected signal for the location, cross-sectional area, volume, and length of any flaws within the test structure using signature analysis.

* * * * *

UNITED STATES PATENT AND TRADEMARK OFFICE
CERTIFICATE OF CORRECTION

PATENT NO. : 4,265,122

DATED : May 5, 1981

INVENTOR(S) : Billy D. Cook; Eduardo Cavanagh

It is certified that error appears in the above-identified patent and that said Letters Patent are hereby corrected as shown below:

Column 1, line 31, change "signals." to --signal.--.
    Column 1, line 54, change "MHz," to --MHz;--.
    Column 2, line 9, change "page" to --pages--.
    Column 5, line 4, change "theorectically" to --theoretically--.
    Column 8, line 31, change "including;" to --including:--.
    Column 8, line 65, change "deflected" to --reflected--.
    Column 8, line 67, delete the indention.
    Column 10, line 22, after "of:", begin new indented paragraph.
    Column 10, line 26, change "non-linear" to --nonlinear--.

UNITED STATES PATENT AND TRADEMARK OFFICE
CERTIFICATE OF CORRECTION

PATENT NO. : 4,265,122
DATED : May 5, 1981
INVENTOR(S) : Billy D. Cook; Eduardo Cavanagh It is certified that error appears in the above-identified patent and that said Letters Patent are hereby corrected as shown below:

Column 8, line 68 through Column 9, line 14, change the formal of Claim 17 to read as follows:

--17. A nondestructive testing apparatus comprising:
an electrical pulse generator;
means for producing and detecting broadband pulses of ultrasonic energy including:
a support,
means for generating a time-domain acoustic ramp signal, electrically connected to said generator, and disposed within said support, said ramp signal dependent upon the shape of said pulse from said pulse generator, and said ramp signal applied to a test structure for evaluation of defects,
a nonresonant broadband receiver disposed on said support for receiving a reflected signal response from said structure; and,
means for evaluating said reflected response.--

Signed and Sealed this

Twenty-fifth Day of August 1981

[SEAL]

*Attest:*

GERALD J. MOSSINGHOFF

*Attesting Officer*  *Commissioner of Patents and Trademarks*